US012478494B2

(12) United States Patent
Johnson et al.

(10) Patent No.: US 12,478,494 B2
(45) Date of Patent: Nov. 25, 2025

(54) SHOULDER BRACE

(71) Applicant: Icarus Medical, LLC, Charlottesville, VA (US)

(72) Inventors: David T. Johnson, Charlottesville, VA (US); Evan Eckersley, Charlottesville, VA (US); Philip Miller, Charlottesville, VA (US); Mason Moore, Crozet, VA (US); Arron Danehy, Charlottesville, VA (US)

(73) Assignee: Icarus Medical, LLC, Charlottesville, VA (US)

( * ) Notice: Subject to any disclaimer, the term of this patent is extended or adjusted under 35 U.S.C. 154(b) by 255 days.

(21) Appl. No.: 18/371,545

(22) Filed: Sep. 22, 2023

(65) Prior Publication Data

US 2024/0009015 A1 Jan. 11, 2024

Related U.S. Application Data

(60) Continuation-in-part of application No. 18/235,319, filed on Aug. 17, 2023, now Pat. No. 12,150,880, and a continuation-in-part of application No. 18/075,203, filed on Dec. 5, 2022, now Pat. No. 11,806,264, said application No. 18/235,319 is a continuation-in-part of application No. 18/075,203, filed on Dec. 5, 2022, now Pat. No. 11,806,264, which is a continuation-in-part of application No. 17/902,683, filed on Sep. 2, 2022, now Pat. No. 11,612,506,
(Continued)

(51) Int. Cl.
*A61F 5/01* (2006.01)

(52) U.S. Cl.
CPC .... *A61F 5/0125* (2013.01); *A61F 2005/0139* (2013.01); *A61F 2005/0165* (2013.01)

(58) Field of Classification Search
CPC ............ A61F 5/0125; A61F 2005/0139; A61F 2005/0165; A61F 13/048; A61F 13/107; A61F 2013/49096; A61F 5/01; A61F 5/026; A61F 5/028; A61F 2/30; A61F 2002/30624
See application file for complete search history.

(56) References Cited

U.S. PATENT DOCUMENTS

| | | | | |
|---|---|---|---|---|
| 10,660,780 | B1 * | 5/2020 | Ostergard | A61F 5/0104 |
| 2017/0281384 | A1 * | 10/2017 | Pimentel | A61F 5/0102 |
| 2021/0205111 | A1 | 7/2021 | Johnson et al. | |

FOREIGN PATENT DOCUMENTS

EP 4011335 A1 6/2022

OTHER PUBLICATIONS

Application No. PCT/US23/33448, International Search Report and Written Opinion dated Mar. 11, 2024.

* cited by examiner

*Primary Examiner* — Tarla R Patel
(74) *Attorney, Agent, or Firm* — Woods Rogers Vandeventer Black PLC; Nathan A. Evans

(57) ABSTRACT

An apparatus and methods for making for shoulder orthoses, which can control the position of the humeral head/arm relative to the shoulder joint by adjusting tension across the joint. The orthoses allows the user to modify the direction and magnitude of force applied while wearing the orthosis. The orthosis may contain cams or extensions to direct and amplify the force around the joint towards a specific range of motion. The orthoses can be made from digitally imaging joints and then partially or fully automating the design of orthosis.

33 Claims, 5 Drawing Sheets

Related U.S. Application Data application No. 18/371,545 is a continuation-in-part of application No. PCT/US2022/021822, filed on Mar. 24, 2022, said application No. 18/235,319 is a continuation-in-part of application No. 17/211,635, filed on Mar. 24, 2021, now Pat. No. 11,819,436, which is a continuation of application No. 17/074,542, filed on Oct. 19, 2020, now Pat. No. 11,564,824, and a continuation of application No. 17/074,571, filed on Oct. 19, 2020, now Pat. No. 12,059,383, which is a continuation-in-part of application No. 15/585,968, filed on May 3, 2017, now Pat. No. 10,806,619, said application No. 17/074,542 is a division of application No. 15/585,968, filed on May 3, 2017, now Pat. No. 10,806,619.

(60) Provisional application No. 63/463,845, filed on May 3, 2023, provisional application No. 63/409,025, filed on Sep. 22, 2022, provisional application No. 62/331,315, filed on May 3, 2016.

SHOULDER BRACE

CROSS REFERENCE TO RELATED APPLICATIONS

The present application relies on the disclosures of and claims priority to and the benefit of the filing dates of U.S. Provisional Patent Application 63/409,025, filed Sep. 22, 2022.

The present application is a continuation-in-part and relies on the disclosures of and claims priority to and the benefit of the filing dates of U.S. patent application Ser. No. 17/211,635, filed Mar. 24, 2021. The present application is a continuation-in-part and relies on the disclosures of and claims priority to and the benefit of the filing date of U.S. patent application Ser. No. 63/463,845, filed May 3, 2023. The present application is a continuation-in-part of and relies on the disclosures of and claims priority to and the benefit of the filing dates of U.S. patent application Ser. Nos. 17/074,571 and 17/074,542, filed Oct. 19, 2020, which rely on the disclosures of and claim priority to and the benefit of the filing date of U.S. patent application Ser. No. 15/585,968, filed May 3, 2017, which claims priority to and benefit from U.S. Provisional Patent Application No. 62/331,315 filed on May 3, 2016. The disclosures of those applications are hereby incorporated by reference herein in their entirety.

The present application is a continuation-in-part of and relies on the disclosures of and claims priority to and the benefit of the filing dates of U.S. patent application Ser. No. 18/075,203, filed Dec. 5, 2022, which is a continuation-in-part of and relies on the disclosures of and claims priority to and the benefit of the filing dates of U.S. patent application Ser. No. 17/902,683, filed Sep. 2, 2022.

The present application is a child application of and relies on the disclosures of and claims priority to and the benefit of the filing date of Ser. No. 18/235,319, filed Aug. 17, 2023.

The present application is a child application of and relies on the disclosures of and claims priority to and the benefit of the filing dates of the following, and the disclosures of the following applications and other applications/patents/literature cited herein are hereby incorporated by reference herein in their entirety:

PCT Application No. PCT/US2022/021822, filed Mar. 24, 2022.

FIELD OF THE INVENTION

The present disclosure relates generally to the field of supporting or correcting joint dysfunction or disorders using an orthosis that allows the wearer to control and modify the direction and magnitude of force across a joint, for example the acromiohumeral joint interval. A method of designing custom orthoses from digital imaging are also described herein.

BACKGROUND OF THE INVENTION

The shoulder is a ball and socket joint and is one of the more complex joints in the body. Additionally, this joint has the greatest range of motion of any joint in the body. Its movement is defined around three axes (a triaxial joint): the anterior/posterior axis, the mediolateral axis, and the longitudinal axis. With two major joints in the shoulder, the acromioclavicular joint and the glenohumeral shoulder joint, the shoulder has six degrees of freedom. Consequently, this range of movement presents a higher risk of injury, as well as a diverse set of injury types. The glenohumeral joint can be dislocated, which may lead to additional medical problems, such as bankart lesions, hill sachs lesions, and humeral avulsion of the glenohumeral ligament. These injuries can present from a range of root causes and underlying conditions ranging from inflammation due to osteoarthritis, to trauma due to impact from sports or other activities. Shoulder pain is a common and disabling complaint amongst individuals with joint pain. The reported annual incidence of shoulder pain is 14.7 per 1000 patients every year and the recovery from these injuries can be slow. Additionally, these recoveries often have a high recurrence of injury. 25% of individuals seeing a physician for shoulder pain have had previous injuries in that joint. Oftentimes the recovery is not fully effective, and 40 to 50% of patients still experience pain after a 12 month follow-up.

One of the most commonly diagnosed issues in the shoulder is subacromial impingement syndrome (SAIS). Moreover, within subacromial syndrome diagnoses, 29% of patients receive a sub-diagnosis of rotator cuff tendonitis, and 12% receive a sub-diagnosis of chronic bursitis. Furthermore, 85% of these patients were diagnosed with general bursitis. These shoulder injuries affect individuals of all ages, but the majority of patients are between the ages of 45 and 64. SAIS affects male and female patients almost equally; 44% of these recorded shoulder injuries were male, whereas 56% were female.

Injuries can cause daytime and nighttime disturbances. 81% of patients have complained about their difficulty in sleeping, with 60% saying they are unable to even lay on their afflicted shoulder.

A common injury for young populations is a torn labrum, while older populations more commonly tear their rotator cuff muscles. These injuries can result from extreme use conditions, as well as general overuse of the joint. Other common issues that cause shoulder pain include shoulder impingement syndrome, calcific tendonitis, frozen shoulder, osteoarthritis, polymyalgia rheumatica, subacromial bursitis, and bicep tendonitis. Such conditions are often only treated with physical therapy or injections, with the most extreme form of treatment being surgery. Shoulder braces present one solution and a part of the continuum of care, which may be helpful in postponing surgery. 28% of patients are advised to forgo surgery for acute injury and seek treatment only after they experience a more severe shoulder injury. As a result, many people end up living with untreated chronic shoulder pain.

Shoulder dislocation injuries often damage the labrum. Once the labrum is torn, the shoulder is at a higher risk of additional dislocations, which can cause further damage. Shoulder dislocation is the most commonly addressed issue by shoulder braces on the market.

In summary, there are a wide range of conditions affecting the shoulder, both acute and chronic, that have correlating impacts on the user's pain and function. However, existing braces tend to simply address the broad range of issues of the complex joint with similar approaches in joint stabilization and limiting range of motion. Athletes commonly use shoulder braces, but the forces associated with joint stabilization in shoulder braces have also been shown to be insufficient and somewhat ineffective. In a study on the effectiveness of existing shoulder bracing as a preventative measure for football offensive lineman, the difference in injury rate with and without the shoulder brace was statistically insignificant. Athletes returning to the season after injury receiving nonoperative treatment had minimally significant outcomes whether or not the athletes were braced or unbraced. Braced athletes returned 80% of the time, while unbraced athletes returned 88% of the time.

In addition, studies show that repeated overhead work, such as painting or carpentry, is affiliated with an increased incidence of shoulder injury and chronic shoulder pain. It has been shown that approximately 58.7% of individuals who often perform overhead work report neck and shoulder pain. In some cases, traumatic injury can occur in the workplace as a result of insufficient shoulder support. Even after shoulder repair or healing, there is likely an incidence of chronic shoulder pain and repeat injury as a result. Regardless, repeated overhead use is linked to degeneration of tendon and bursa tissue in the shoulder, which results in chronic pain, reduced activity and loss of the ability to work. One study showed approximately 30% of all workers that report shoulder pain take at least one day of sick leave. Those that remained at work with the shoulder pain had persistent symptoms, ultimately not allowing their injury to recover. In another study, 41% suffering from neck and shoulder pain reported sickness absence of at least 14 consecutive days.

While there are clear correlations between specific activities and careers and incidence of shoulder injury, solutions on the market fail to address this reality. Existing braces on the market either provide compression or statically limit range of motion in order to reduce pain. These, often off-the-shelf products do not specifically support the user's required motion or treat the root causes of their shoulder irritation. In addition, such braces can often loosen during activity, further reducing the efficacy of the brace. Migration or loosening can be due to the material, the method of adjustment, or the lack of custom-fit of the existing braces on the market. At the same time, exoskeletons designed to augment the shoulder during activity are highly expensive and lack adjustability by the user, and they are therefore inaccessible to the majority of the population that would benefit from such a device. Furthermore, the high-weight and high-power requirements of exoskeletons make them less viable for broad use. There is a significant, unmet need for an effective, accessible, adjustable and customizable shoulder apparatus that can adjustably support, limit, or augment the joint during a range of activities, users, and conditions.

DESCRIPTION OF RELATED ART

The primary use of existing shoulder braces on the market is to limit shoulder mobility to address the dislocation of the shoulder and postpone inevitable shoulder surgery. These braces create stability in the shoulder joint, but are often uncomfortable and do not fit properly. The two most common types of shoulder braces include sleeve braces, commonly made of neoprene or other elastomeric material, and immobilizer braces.

Sleeve braces found on the market are focused on compression as well as stability. These braces are form fitting to the upper body and apply forces securing the shoulder joint into place. By employing adjustable and elastic straps shoulder mobility is limited, keeping the joint from further damage.

The company Flawless Motion™ sells different styles of sleeves, a multidirectional shoulder brace, and an anterior shoulder brace. These styles are also available in a bilateral shoulder brace style. In addition, Flawless Motion™ sells an acromioclavicular joint brace and a rotator cuff brace. Flawless Motion™ supplies braces for both men and women; however, a major complaint with these braces is the poor fit on women patients. When the Flawless Motion™ braces are completely secure, the fit can be uncomfortable and is difficult to apply by the patient themselves. https://flawless-motion.com/

ARYSE® offers customizable shoulder braces. They offer two variants of the shoulder brace: the SFAST® and OSKIE®. The OSKIE® brace is a sleeve design that allows for a larger range of motion while also giving support. To customize the brace to achieve the most beneficial support, the design can be changed to address anterior instability, posterior instability, or multidirectional instability. Made with nylon, neoprene, and rubber, it provides compression while being lightweight. The applications include muscle strains, post-surgery recovery, joint instability, and subluxations. https://aryse.com/shop/exo-performance?gclid=Cj0KCQiAq7COBhC2ARIsANs PATEAVb1oVvCTYMRVNUJJIWRfoGt3 gpSSdvBcmrYcSHvXiePGKZX1LSAaAgrREALw_wcB The Sulley™ brace by DonJoy® is one example of a sleeve brace on the market. These braces address instability of the acromioclavicular joint as well as general joint instability. Made from an adhesive neoprene in a vest format, the brace is less likely to migrate during use. It employs a universal design for both the right and left shoulder. Allowing for many custom fit applications, the brace gives the user a sense of stability in the shoulder joint. However, the brace has been shown to lack effectiveness in certain clinical indications. Even after wearing the brace, some users have experienced shoulder dislocations causing further damage to the joint. In addition, the brace can be very difficult to .don and doff alone or when wet. https://www.donjoyperformance.com/saunders-sully-shoulder-support The immobilizing shoulder brace is another on market technology that has been effective for some patients. This brace is significantly more bulky, but limits mobility to a greater extent. The increased stability from the brace has been shown to be more effective in limiting shoulder dislocations and ultimately decreasing the likelihood of further damaging the joint. The SFAST® brace by ARYSE® is a form-fitting brace, with the bulkier immobilizer straps to add securability. This brace uses polyurethane straps that "mimic" the body's natural movement. With 360 degree customizable support, it offers help with anterior and posterior instability. https://aryse.com/product/sfast/?gclid=CjOKCQiAzMGNBhCyARIsANpUkzPq0D-AZG6_doqigObtI11wKZKePEqBABFAm64xLPVs0du hkgBfilMaAkfbEALw_wcB Breg® and DonJoy® both make stabilizing/immobilizing shoulder braces. The DonJoy® brace provides shoulder immobilization with a controlled range of motion. It helps protect and stabilize the shoulder before and after operation. It can be worn under sports protective gear and features abduction control. While this brace offers stability and motion control in the joint, the fit of the brace is bulky and uncomfortable. Additionally, this brace can be difficult to run with. This brace is most effective in sports that require players to already be wearing protective pads, such as football or lacrosse. This brace loses effectiveness and migrates more often when used for sports such as soccer or rugby. https://www.donjoyperformance.com/donjoy-shoulder-stabilizer?medium=tsa&gclid=Cj0KCQiA2sqOBhCGARIsAPuPK0i_Ck6dVVFItZL_ymeHdED 30hbgv7s6iw-S3XGoL2HgLFvqU7xfdzcaAuJBEALw_wcB&gclsrc=aw.ds Breg® stabilizing braces limit abduction and external rotation, while maintaining functionality of the joint. It is easy to fit and harness with a universal left and right arm design. The chest and cuff regions of this brace are very minimal. The chest only focuses on the upper chest area, covering less than ⅓ of the body. The cuff design has only one strap connecting it to the chest area. With the minimalistic design, it can achieve good fits because of the lack of contact area on the user, but does not allow for much adjustability for the stabilization of the joint. https://www.breg.com/products/shoulder-bracing/immobilizers-stabilizers/shoulder-stabilizer/

While shoulder braces are generally used for pain management, there is a lack of bracing used for preventative care. Some companies have developed exoskeletons to protect the shoulder during overhead work by limiting range of motion and providing stability.

While they do offer some support, they are bulky, expensive, and inaccessible to everyday people. Often, such braces run $3900 or more and are not covered by standard insurance. Only a limited number of companies offer such solutions to their employees due to this cost, as in the case of the EksoVest™ and the Paexo-shoulder to limit strain on the shoulder. There is a need for a more cost-effective, minimal brace that can be personalized to the user's specific functional need in their line of work that is accessible to the millions of workers in the industry.

Other braces in the field are for immobilization or rehabilitation of the joint through a variety of methods, Other shoulder braces, such as the one described in U.S. Pat. No. 7,255,679 have used tensioning elements to secure the shoulder joint, such as a tensioning ring or tensioning straps. However, this tensioning element is used to provide compression when the joint is moved beyond a safe range of motion zone. The brace does not give the user the ability to adjust tension in real time, and the forces applied are for compression rather than stability. Another brace, such as the one described in the patent application US Patent Publication No. 2017/0281384, uses tension to treat shoulder injuries by applying compression as well. This brace is donned by the user and then through a tensioning element it can be compressed on the arm of the individual to apply a snug fit. This allows for an easy way to don the brace, but the adjustable tensioning element is only used to address the lit of the brace rather than providing significant clinical function. The tensioning element of this embodiment does not control or affect the forces being applied to the shoulder in order to restrict mobility.

SUMMARY OF THE INVENTION

The shoulder brace disclosed herein in this Application has numerous advantages over the braces mentioned above in conservative care of acute or chronic conditions, post-operative application, or assistive application for injury prevention. The current invention described herein provides multiple features that offer customization and tenability to the specific user need and clinical indication. In aspects, the current incorporates a tensioning or compression system that can adjust both the direction and magnitude of the force applied by the brace to immobilize the shoulder. With a tensioning element installed in the brace according to the current invention, the user can easily modify the magnitude of force while wearing the brace. In addition, the tensioning element according to the current invention can be positioned in a wide variety of locations such that the user can easily change the director of force within or around the shoulder joint. According to the current invention, the user can feel the difference when the brace is applied and adjust the magnitude of force as needed. This amount of assistance according to the current invention can be changed based on pain level, desired activity, or user preference. According to the current invention all of these changes can be performed by the user while keeping the brace on, allowing for ease of use. In post-operative applications, the brace described herein can be adjusted based on the user's rehabilitation needs or stage as prescribed. In aspects, elements under compression (described herein as compression elements), may be incorporated in combination with the tensioning elements to distract or unload the joint in specific regions or during a specific range of motion.

In aspects, the disclosed shoulder brace also provides the advantage of using a 3D scan of different sections of the user's upper body to optimize fit and distribute forces evenly. The custom components can be manufactured using 3D printing to optimize the strength-to-weight ratio. This also provides an additional functional advantage of varying device or component rigidity in different regions to better accommodate the properties and variability of soft tissue. In embodiments, the ranges of forces applied can instantaneously and easily be changed by adding or substituting the elastic or spring elements of the tensioning mechanism with different materials of different tensile properties. Connections between the cuff and chest regions are established through the cabling system of the tensioning mechanism. In other aspects, different anchor points established on the shoulder portion or cuff of the brace will direct the path of the tensioning system, allowing the user to change the direction and magnitude of the forces around, between or within the shoulder joint.

In embodiments, the device described herein is a multi-axis rotation control shoulder orthosis that can stabilize and control forces around the shoulder joint and may optionally be customized to the user's need. This orthosis is used to relieve pain, enable certain movements while restricting others, enable certain activities, augment movement, and prevent future injuries. The orthosis can be designed to allow for a significantly greater degree of personalization and tuning to an individual's specific need through 1) customization of fit and modularity, 2) adjustability by the user of the magnitude of forces generated around, across, between or within the joint, and 3) adjustability of the direction of threes and the net force around, across, between or within the joint compared to existing orthoses on the market. The personalization and adjustment of the orthosis can be achieved by the user while wearing the device, the manufacturer or the clinician through multiple unique features including 1) a tensioning or compression element, which stores energy in one or more directions across or around a joint 2) an adjustment mechanism for changing the amount of energy stored and resulting force within the tensioning or compression element, 3) optionally, a mechanism of changing the direction/orientation of corrective force(s) through a series of anchors, slots, or other positioning elements and 4) optionally, a method to custom-fabricate the device to optimize the comfort and efficiency of the device's form based on the anatomy of the user.

In order to control the rotational and/or translational forces on the shoulder in one or more axes, the device may contain one or more tensioning or compression elements to address the user's need. One or more tensioning or compression elements may be controlled by a single adjustment mechanism (or more than one). These elements may be modular, and can be added or removed as needed based on the user's condition. Multiple elements can be used in this orthosis to introduce more forces in different directions to secure the shoulder joint. The adjustment mechanisms can be comprised of the same components, or have varying components and designs. These designs include rotary dials, levers, ratchet and pawl mechanisms, and the like. In one embodiment, adjusting the component (either adjustment mechanism, tensioning or compression element, or anchors) changes the direction of the forces. (For example, moving the location of an anchor point). In another embodiment, adjusting the component changes the magnitude of the force applied (for example, stretching an elastic or spring element). Combining these embodiments would allow for adjustments that change the direction of the force as well the magnitude. The energy storage elements used in conjunction with the adjustment component can be changed to affect the strength, location, and orientation of the forces. In embodiments, the anchors may be constrained to move on a track system on which the anchors can slide when unlocked. The anchors can be securely locked at specific discrete positions on the track in order to alter the direction of force generated by the tensioning system. For example, the track may allow for anchors to be adjusted in 10° increments from the anterior to posterior orientations around the shoulder joint. The track system may be located on the arm portion, the body portion, or both.

In an embodiment, the orthosis is composed of two pieces: the arm portion and the body portion. The arm portion of the brace can be attached around the bicep of the individual while the body portion is generally around the upper portion of the upper body and chest region. These two portions are connected through the tensioning system. This tensioning system has a series of pipes or guides connecting both portions with the tensioning cable within the pipes. These cables can have an elastic feature in series with them to create the pressure on the shoulder joint forces that keep the joint in place. Another embodiment involves the tensioning system integrated within clothing or equipment such as a jacket or football shoulder pads, where three is manipulated between the torso and humeral components to restrict, limit or facilitate movement of the shoulder and/or arm. The arm portion may optionally be connected by a flexible (e.g. fabric) portion in addition to the tensioning system. In embodiments, the flexible portion may comprise channels or house the tensioning system.

In aspects, the tensioning element is completely adjustable. As a non-limiting example, with the rotation of a convenient dial, the magnitude of force can be changed between one or more magnitudes of force. Other adjustment mechanisms, such as a slider, a toggle, a selector, a ratcheting pull strap, or the like, could be envisioned. The larger the magnitude of the force applied, the greater the shoulder joint immobility within the brace. By shifting the anchor points of the stored energy element to the brace, the direction of the forces can be changed. Anchor points on the brace can be easily moved from one point on the brace to another. The cable can be moved to existing points on the brace locked into place to change the direction of the force. The direction of force applied by the cabling system attached to the tension element is easily manipulated through these moving anchor points. The cable is defined as any flexible element that can support a tensile force and by example includes lace, wire, rope, fishing line or the like.

The tensioning element in the brace can be used to supply forces around, between, across, or within the shoulder joint (and more specifically any axis of the shoulder joint) to ultimately prevent dislocation, or limit the likelihood of dislocation, and minimize movement that will aggravate the target region of the joint. Through a combination of anchor points and tension from the energy storage element (defined as a tension element, compression element, or any element that stores energy under tension or compression), different force vectors can be achieved through the brace. This allows for users to change their desired force exerted on their joints. It allows the user to subject a force axially to pull the joint proximally, or distally, or both if needed depending on how the adjustment is applied. In the same way, the device may translate the shoulder in anterior, posterior, superior or inferior direction. In this manner, the orthosis described by this invention protects the shoulder from further damage from dislocations.

It is envisioned that the shoulder orthosis could be connected to or used in conjunction with additional orthopedic or prosthetic devices using universal connectors. This shoulder brace can be connected to other braces such as an elbow, and/or wrist/hand brace, and/or back brace, and/or a neck brace to further the utility of the brace in conjunction with other orthoses. Any one of these orthoses may contain a similar adjustable tensioning mechanism, which can be used individually or adjusted with a single connected adjustment mechanism. Such connectors may include load distributors, which are designed to distribute forces generated by the tensioning or compression systems on the arm or chest.

The tensioning system can translate tension beyond the shoulder brace to other body parts through anchors and/or ports that impart forces on the joint(s) in the desired way. Tension-generating devices are not limited to the shoulder. This concept has been used in the knee and ankle braces made by Icarus, and can similarly be applied to other body parts, limbs or joints. The independent elbow joint brace for example will function like the knee brace to either facilitate flexion, extension or rotation. The wrist brace will facilitate or restrict ulnar-radial or plantar-dorsiflexion. The brace may further extend to the hand and fingers of the user. Each segment (shoulder, elbow, wrist, hand) may incorporate independently adjustable tensioning or compression elements and individual mechanisms to control forces in and around that joint or body part. The back and neck braces, for example, may support the joint while generating tension in a transvertebral direction, across one or more vertebrae, to unload a portion of the joint, shift forces/weight from one part of the joint to another, move two parts of the joint, and/or create a rotational force about the joint. The force can be static or dynamic, increasing with increasing motion, and can be adjustable by the user in advance of wearing or while wearing the device. The brace can take advantage of different morphology between two body parts to impart a three across the two joints, and this force can be a pulling or pushing force, or a compressing or distracting force. The back brace using this concept may pull in one or more directions, while also pushing in other directions, to create the desired system of forces to improve the function of the joint and/or relieve pain. A similar system can be employed on the hip, and may be connected to other bracing, such as in a hip-knee-ankle foot orthosis (HKAFO). The same mechanisms may be applied to prosthetics, either with the prosthetic arm or hand device incorporating the described tensioning systems, or the prosthetic devices being used in combination with the described shoulder and combination upper extremity orthoses.

One embodiment of this design is a more flexible shoulder orthosis that would be made of elastic form-fitting material. This embodiment lays sleeker and more discrete on the shoulder without sacrificing much of the strength and stability provided by a rigid brace. The form fitting elastic material will provide a large amount of compression on the joint and keep the joint secure and stabilized. This embodiment has the advantage that it will not be noticed underneath clothing because it is thin and form fitting. This minimalist embodiment of the shoulder orthosis includes but is not limited to the tensioning element, channels or piping for the tensioning cables, the elastic materials for tension, and the form fitting orthosis that covers the upper body. Yet another additional benefit of the brace described herein is that it can more precisely assist or support the joint in at least one plane, targeting the area of the joint most needing support, so that the risk of atrophy for supporting muscles and ligaments may be reduced.

The various embodiments of the present disclosure may use traditional manufacturing processes for other shoulder braces, and/or 3D printing to produce the components. They may also be used to fabricate positives through which negative molds are constructed for molding.

The fabrication technique allows low-cost, custom devices. It also enables manufacture of intricate parts containing internal channels and features that could not be feasibly or affordably produced with injection molding, machining, or other traditional methods of manufacturing orthotic devices. 3D printing enables efficient production of lightweight, yet durable materials. The result is a highly effective, lightweight, customized, and cost-effective device that can be manufactured at scale.

Using a 3D scan, components of this shoulder brace can be customized and fabricated for the user/wearer, Different portions of the brace can be rigid or flexible, with the intent to customize the fit of different parts of the upper body to create the best fit of a shoulder brace. Anchor points for the tensioning system can be custom fabricated from the patient's scan. Alternatively, they can be assembled on the arm portion, the body portion or the tensioning system in a custom manner based on the scan or other patient information including prescribed device or clinical indication. These anchor points can include locations on, hut are not limited to, the bicep region, the tricep region, the chest region, the shoulder blade region, the neck/cervical region, and the abdominal region.

The 3D scan can be used by a designer, clinician or fabricator to manually, automatically, or semi-automatically fabricate a custom device through 3D printing. This custom fit will optimize the comfort of the brace and will maximize the device effectiveness by increasing contact area on the patient by evenly distributing the forces on the body part. For example, a plate that is customized from the 3D scan on the bicep will have high tension forces from the tensioning element. Having a custom fitting portion in this region will allow for these forces to be evenly distributed in the area. This even distribution will be more comfortable and will apply the forces in the correct direction to secure the shoulder joints. It is envisioned that the device can be wholly or partially prefabricated and can be further modified by the user or a professional to provide the desired function. This modification can include but is not limited to thermoforming of the rigid components to improve fit, comfort or function. Adjustments and modifications of the anchor points for the tensioning element can be used to create the correct direction of the force.

BRIEF DESCRIPTION OF THE DRAWINGS

The accompanying drawings illustrate certain aspects of some of the embodiments of the present invention and should not be used to limit or define the invention. Together with the written description, the drawings serve to explain certain principles of the invention.

DETAILED DESCRIPTION OF THE INVENTION

The present invention has been described with reference to particular embodiments having various features. It will be apparent to those skilled in the art that various modifications and variations can be made in the practice of the present invention without departing from the scope or spirit of the invention, One skilled in the art will recognize that these features may be used singularly or in any combination based on the requirements and specifications of a given application or design. Embodiments comprising various features may also consist of or consist essentially of those various features, Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention. All references cited in this specification are hereby incorporated by reference in their entirety. As used herein, the term "proximal" is synonymous with top or upper, as in above the shoulder. The term "distal" is synonymous with bottom or lower, as in below the shoulder. As used herein, the term "anterior" refers to the front of the shoulder, body, or device while "posterior" refers to the back. The term "inferior" refers to below a region of the body while "superior" refers to above a region of the body. Throughout the following detailed description, it should be understood that elements in tension are by example and that the same rotational force may be generated by a compression element on the opposing side of the shoulder. It should also be understood that the adjustable tensioning and compression apparatuses herein are described in shoulder orthoses by example only. According to the current invention, similar adjustable tensioning and compression apparatuses could be applied to control rotation and forces around other joints including the wrist, shoulder, back, neck, knee, hip, ankle and elbow. For example, the adjustable tensioning apparatus described herein could be used in an assistive knee orthosis. Throughout the following detailed description, the same reference numbers refer to the same elements in all of the figures.

Preferred Embodiment One: Shoulder Brace with Arm and Chest Portions

Figure 1A:
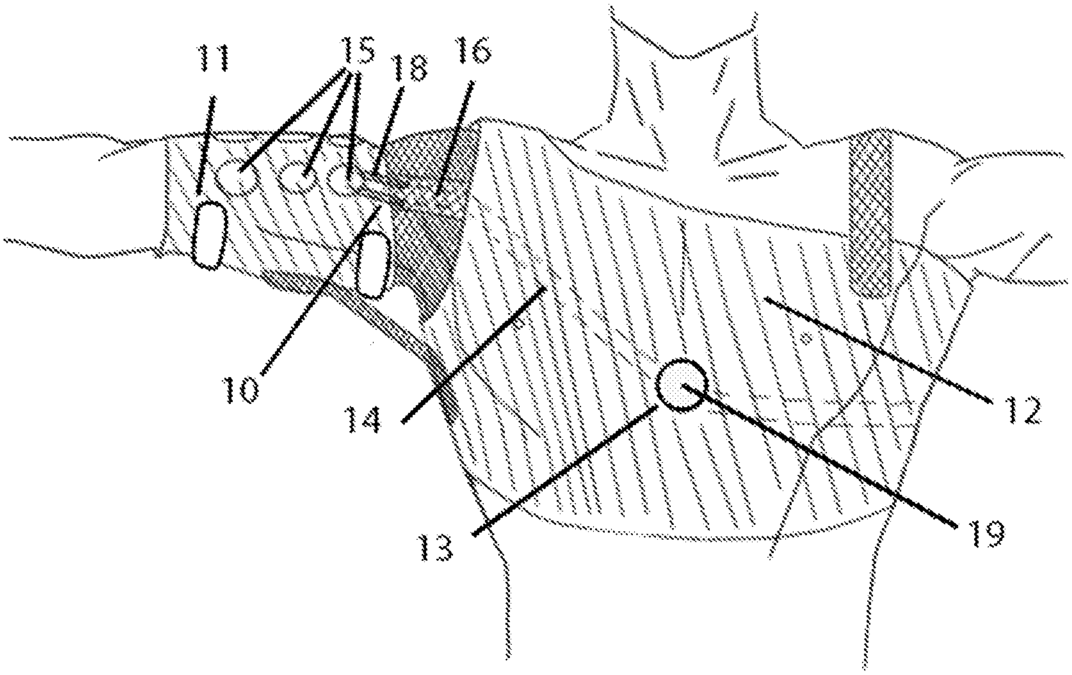
FIGS. 1*a* and 1*b* are illustrations of front and back angles, respectively, of a shoulder brace with the tensioning element and cable system according to an embodiment of the invention described herein.
Figure 1B:
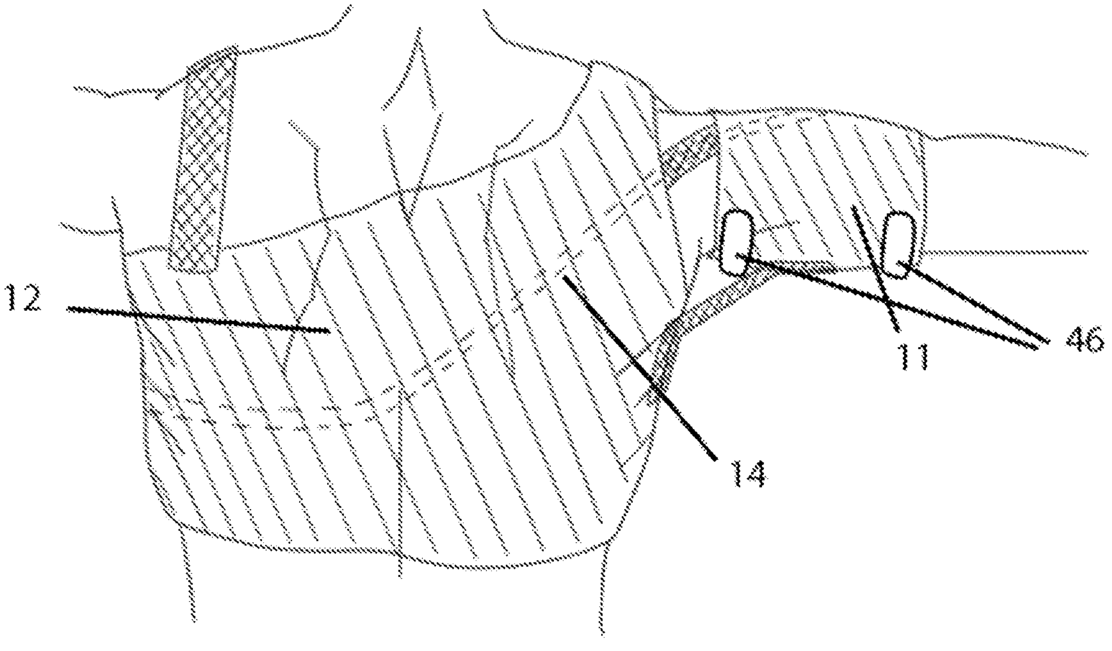

FIGS. 1*a* and 1*b* show an embodiment of the invention is a shoulder brace comprising at least two separate aspects, the cuff (11) (an example of the arm portion) and the chest strap (12) (an example of the body portion). These two components are connected through a strap system (16) which further comprises a tensioning element (10). The tensioning element in combination with a cable (114) and adjustment mechanism (13) further comprises a tensioning system (10), wherein the cable optionally connects the tensioning element to the adjustment mechanism. In this embodiment and other embodiments described, such cables, lace or cable systems (14) function to operationally connect components of the device including the arm portion, body portion, tensioning element, adjustment mechanism or other modules of the device.

The cuff design (11) of this embodiment of the brace can be secured around the bicep, elbow or forearm of the user. The cuff (11) may be designed to prevent migration up or down the arm, for example as a semi-rigid sleeve with an upper diameter that is greater than the lower diameter. Additionally, the cuff (11) may comprise straps (46) that allow the user to tighten, loosen, rotate or generally position the cuff securely on the arm. In embodiments, the cuff is secured on the arm of the user, for example, with a strapping system, close to the shoulder and on the bicep muscle. The cuff may optionally comprise different anchor points (15) that the elastic element of the tensioning mechanism can attach to. This attachment point (32) of the cables can be made of an elastic or inelastic material; however, in this embodiment it is connected through an elastic element of the cable system. These variable anchor points (15) give the ability to change the direction of the force used to secure the shoulder joint. With the variable anchor points, the user can adjust the tensioning element to where the joint feels the most secure. The cuff (11) can also attach to the body portion (12) through an optional strap (54) to add more strength to the system.

In embodiments, the cuff can have a 3D printed rigid or semi flexible portion (22) produced from a 3D scan of the arm. This plate (22) can be used to distribute the forces from the tensioning element. The described custom element can be 3D printed with the different anchor points (31) on the plate. (See, e.g., FIG. 3.) If this portion is printed with a rigid material, the anchor points are strengthened. The fit of this optional plate (22) will conform to the arm of the user because it is made from the 3D scan. This optimal fit allows for a comfortable shoulder brace that is effective in minimizing the mobility of the joint.

This aspect of the shoulder brace contains the tensioning element (18) used to apply forces on the shoulder joint. As stated above, it can be attached to the cuff (22) through strapping (46) and the cable system (14) of the tensioning element. The tensioning element (18) is attached directly to the brace, and can be removable, or permanent. If the tensioning element (18) is removable, the tension is locked in place when the element is removed.

Figure 2A:
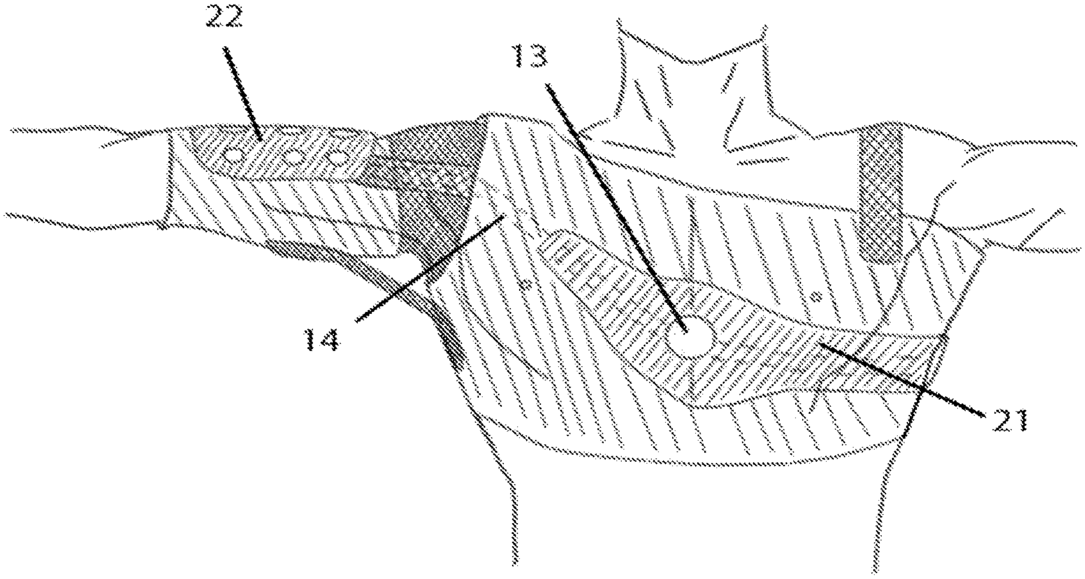
FIGS. 2*a* and 2*b* are illustrations of front and back angles, respectively, of the shoulder brace with custom plates according to an embodiment of the invention described herein.
Figure 2B:
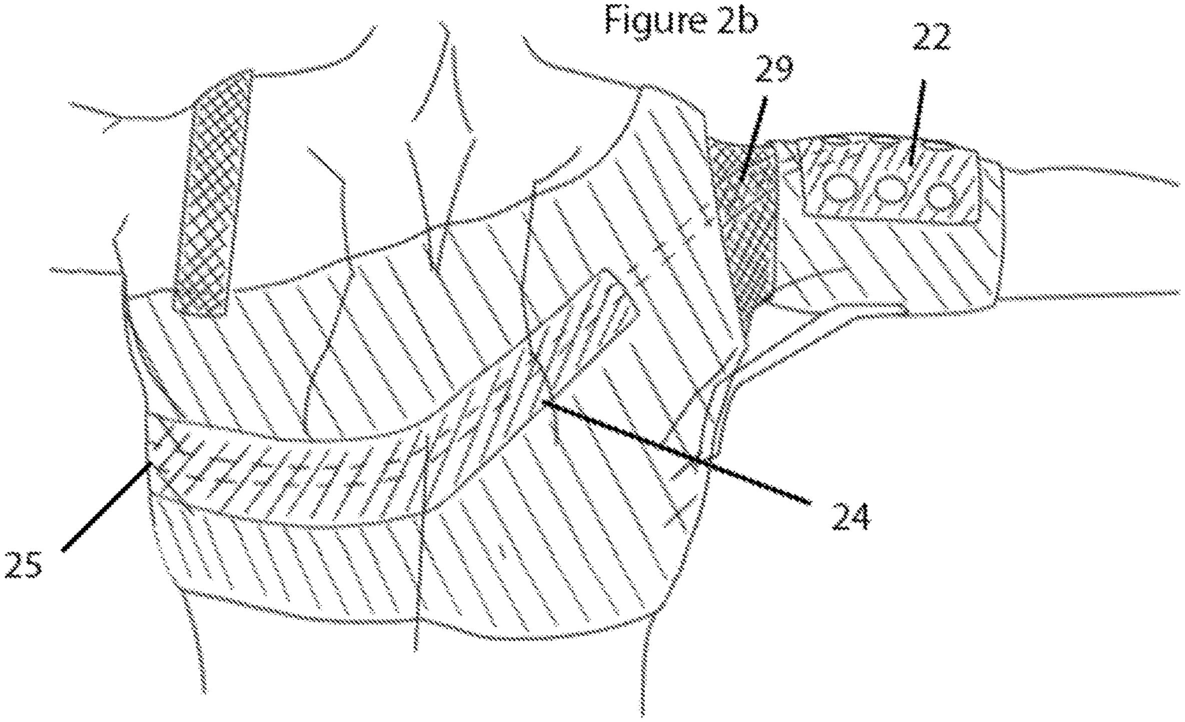
Figure 3:
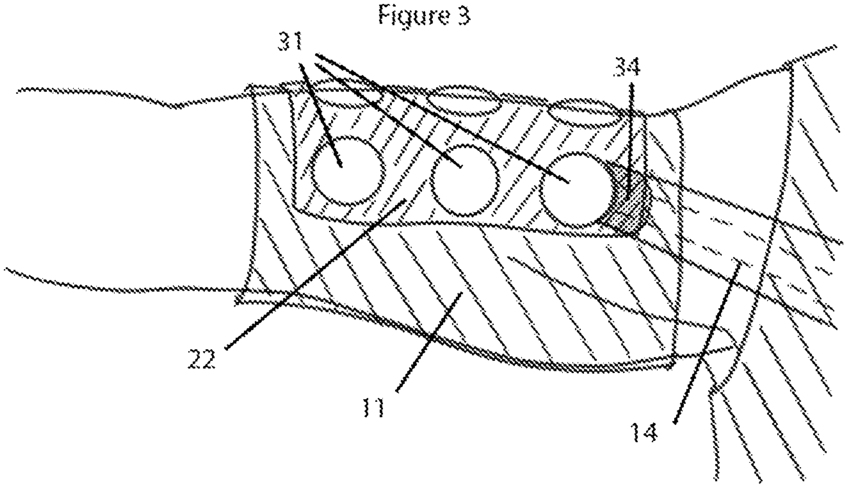
FIG. 3 is a depiction of a cuff aspect with optional plates of the brace with different anchor points according to an embodiment of the invention described herein.

In aspects, as shown for example in FIGS. 2 and 3, the majority of the cable system (14) for the tensioning element (18) is attached on the chest part of the brace (21). This cable system (14) can be attached on one side to the rotary tensioning system, and attached to an elastic material (34) on the other side. As mentioned above, the elastic material can be secured into the cuff anchor points (15). The cable system can be a series of channels or guides (29) for the inelastic cable to go through without being exposed. This cable system can run through the front to the cuff part of the brace to pull the arm forward. This limits the mobility of the shoulder backwards. In addition, the cable system can be run around the back to the arm to pull the joint backwards and limit the mobility of the shoulder with its forward movement.

In embodiments, as shown in FIGS. 2*a* and 2*b* and FIGS. 5*a* and 5*b*, for example, the chest part of the brace (21) has straps to fit the brace (52) to the chest area. These straps (52) can be tightened or loosened depending on the fit of the brace on the user. In addition, optional elements (31) can be attached to this chest area similar to the cuff (22) area. In this embodiment, they are illustrated similar to panels or plates (24). These elements can be used to change the anchor points (31) of the cabling system (14) as well as to distribute the forces on the chest area (12) due to the tension in the cable system. These elements can be made using a 3D scan of different, chest areas and printed using a 3D printer. These elements will conform to the user well due by employing the scanned chest areas to custom fabricate the units. This will increase the surface area in contact with the user, spreading the forces evenly through the element. These elements can be, but are not limited to, attached to the abdominal region, the inside shoulder region, on top of the shoulder, on the lower hip, and on the shoulder blades.

With the tensioning element (18) (see, e.g., FIG. 1*a*) pulling on either side, the shoulder joint is restricted. If the mechanism is attached to the front of the cuff (22) (see, e.g., FIG. 2*b*), the shoulder is then translated in the anterior direction. This ultimately limits the shoulders ability to move in the posterior direction and unloads a posterior region of the joint. The opposite would apply if the mechanism is connected to the back of the cuff, providing a force in the posterior direction. When the tension on the cuff (22) is pulling it posterior direction, due to the cuff (22) being attached from the back, it limits the ability of the shoulder joint to move forward. (See, e.g., FIGS. 2*a* and 2*b*.) In addition, both of these orientations are pulling the shoulder joint down and into the body. This secures the joint in place by limiting the movement of the joint in the superior direction.

Preferred Embodiment Two: Form Fitting Brace

Figure 4A:
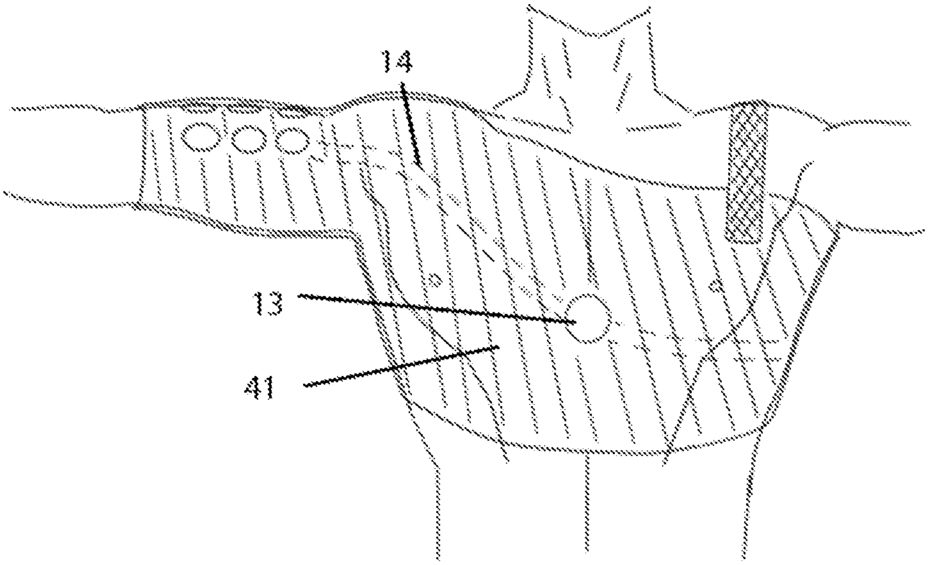
FIGS. 4*a* and 4*b* are illustrations of front. and back angles, respectively, of a form fitting shoulder brace with a tensioning element according to an embodiment of the invention described herein.
Figure 4B:
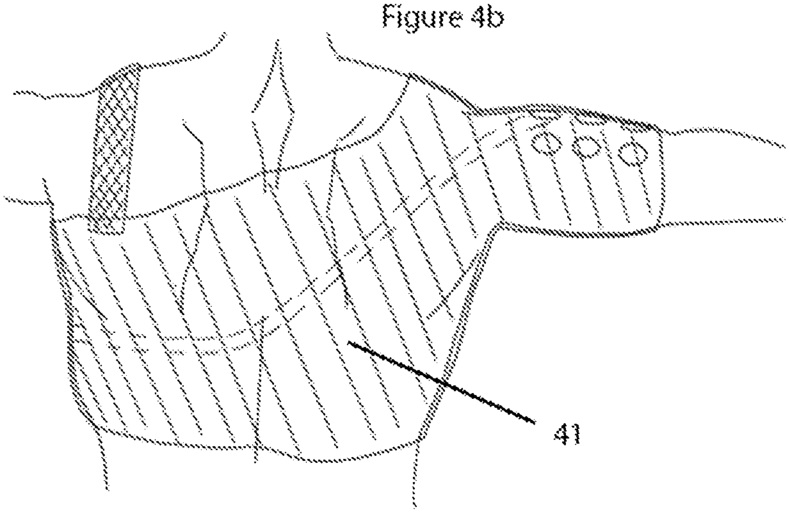
Figure 5A:
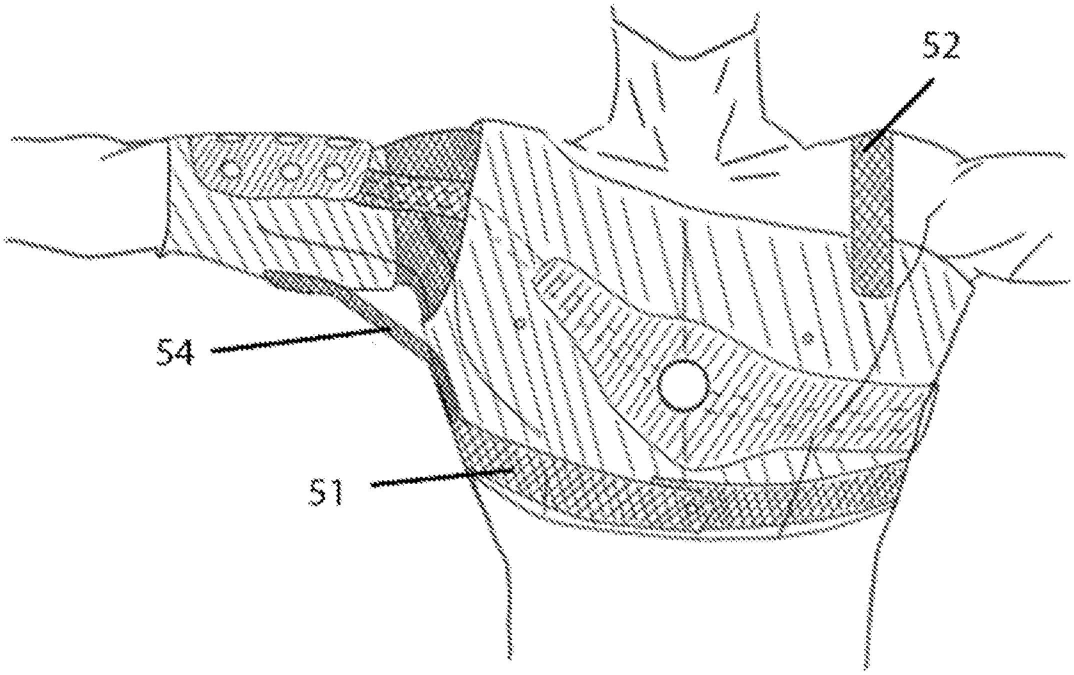
FIGS. 5*a* and 5*b* are illustrations of front and back angles, respectively, of a shoulder brace with optional and additional fitting straps according to an embodiment of the invention described herein.
Figure 5B:
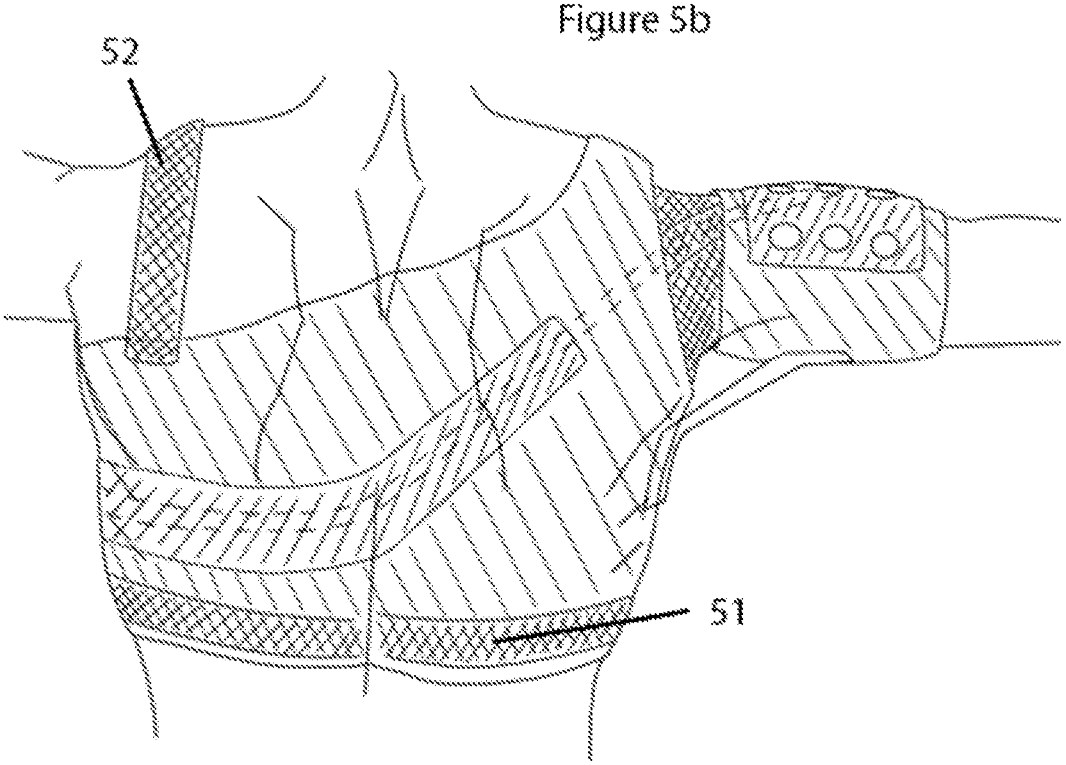

Another embodiment of this brace is a form fitting shoulder brace (41) with a tensioning element. (See, e.g., FIGS. 4*a* and 4*b*.) This design can be worn easily and discreetly under clothes while also maintaining strength and security in the joint. This form fitting brace also provides compression on the joint. In this embodiment, the cuff and chest region can all be one piece. The brace fits like a piece of clothing. With the arm in the arm portion cuff region and the user's chest inside the body part/chest part of the brace, it is securing the joint in place.

This brace can use the tensioning system (10) described in the above embodiments. The channels for the cable system (29) (see, e.g., FIG. 2*b*) can be incorporated into the form fitting brace or it can be positioned on the outer surface of the brace, There can be an elastic element (34) attached to the cuff region of this brace. When this region is under tension it keeps the shoulder joint in place.

The form fitting brace secures the joint in a similar fashion as the previous embodiment. When the elastic piece (34) (see, e.g., FIG. 3) is anchored on the front of the cuff and is pulled under tension, it limits the backwards movement of the shoulder. When the elastic piece is anchored on the back of the cuff, the shoulder's ability to move forward is limited. The forces can be employed at the same time or separately. It is preferred that the forces have a vector that is primarily in the downward direction, limiting the movement upwards.

In aspects, the tensioning element (18) is a key element of this brace. With this tensioning element, the brace allows the user to adjust the amount of immobilization of the joint. For example, twisting the dial (19) can increase or decrease the amount of tension in the system, ultimately changing the forces on the shoulder joint. The tensioning element (18) pulls the shoulder joint in the chosen direction to limit mobility and keep the joint in place. These forces are what keep the shoulder from further damaging itself due to dislocations. (See, e.g., FIG. 1*a*.)

In aspects, the cable system (14) that is attached to the brace and the tensioning element (18) connects the arm piece to the chest piece of the brace. Substantially inelastic cables run inside small channels (29) that are either located internally or are positioned along the outer surface of the brace. The cables are anchored to the adjustment mechanism (13), for example, a rotary element, attached to the chest piece (21) of the brace. The other end of the cables are anchored on the arm portion/cuff part (22) of the brace. (See, e.g., FIGS. 1 and 2.) This piece that is anchored on the cuff (22) can be made of a combination of elastic (34) and inelastic (16) materials that attach to the cuff. Different anchor spots (31) of this cuff (22) can change the direction and magnitude of force being applied to the shoulder. (See also, FIG. 3.) This gives the user the ability to customize the degree of security and immobilization they want with the brace. It is envisioned that the user can further customize the orthosis by replacing the elastic element with other elements with different properties to fine tune the forces applied by the cabling system. Elastic material can be exchanged for other materials that have different tensile properties. This gives the user more ability to customize their fit and strength of the brace.

Another advantage of the invention is that braces can be donned by the user without tension applied making it easy to put on or take off. Once the brace is put on by the user, the tension can be adjusted up or down by the user/wearer. This can be varied for different activities in real time. This gives the user the ability to adjust the forces on the joint depending on how it feels when secured in the brace.

Preferred Embodiment Three: Multi-Axis Rotation Control Shoulder Brace with Arm and Body Portions Connected by a Tensioning Element Another embodiment is comprised of a proximal body portion (12) (e.g. a chest strap (51)) and distal arm portion (11) (e.g. a bicep cuff). (See, e.g., FIGS. 5*a* and 5*b*.) The device contains an adjustable tensioning system (10) that connects the body portion and the arm portion. The tensioning element represents one type of energy storage element, in this case under tension. The tensioning apparatus in this example further comprises a tensioning element (18), a rigid cable (14), and an adjustment mechanism (13). The adjustment mechanism, in aspects a rotary dial, is embedded in an adjustable mechanism insert within the body portion. It may be held in place by the form of a locking mechanism, where the dial's (19) male end is complementary with the female insert in the body portion. It may be sewn or glued or otherwise bonded into the body portion. Regardless of the method, the adjustable mechanism insert (13) can ensure that the adjustment mechanism is securely in place when subjected to any force generated intentionally or inadvertently by the user, including but not limited to rotation in either direction, or pulling out. The adjustment mechanism (13) is functionally connected to one or more cables (14), for example by a knot. The term cable herein generally refers to any type of cable, wire, braid, string, chain, lace, rope, or article that is substantially flexible yet not extensible and is able to be wound up and transmit tensile forces.

The cable or cables (14) may optionally be attached to the one or more tensioning element, which is inserted into the arm portion, and may be anchored in a slot within the arm portion. When tension is applied to the tensioning element, the arm portion is pulled towards the body portion. As shown in embodiment three, this would generate a torque around the top of the shoulder joint. It would also generate a force pulling the arm into the shoulder or more specifically the glenohumeral joint, e.g. providing a compressive pressure within the glenohumeral joint. Anchoring the tensioning elements in other positions around the joint (e.g. anterior or posterior to the joint) would provide a different direction of net force around the joint, Such force could supplement muscle, tendon or ligament function, or limit range of motion in a desired direction.

The adjustment mechanism (13) can allow the wearer/user to change the magnitude of force within the tensioning element, and therefore the force around the joint based on their need. In some embodiments, the adjustment mechanism allows tension to be increased in one direction, e.g., by clockwise rotation of a dial. The tension may be released rapidly by disengaging the dial, e.g., by pulling it out, pushing it in, or pressing a button. In other embodiments, the adjustment mechanism may allow gradual increase or decrease of tension. For example, clockwise rotation of a rotary dial would increase tension, while counterclockwise rotation of the dial would reduce tension. The adjustment mechanism (13) may be a rotary dial, a lever, a switch, a ratchet and pawl mechanism, a pulley, or an electronic adjustment mechanism operated by a controller and/or a motor. The adjustment mechanism may be placed in a preferred position for use that is non-obstructive during activity, but accessible, for example at the rear of the body portion.

Preferred Embodiment Four: Multi-Axis Rotation Control Shoulder Brace with Body Portion and Arm Portion Connected by a Hinge Another embodiment is comprised of a body portion and arm. portion connected by one or more hinges and a tensioning apparatus. Unlike embodiment three, the body portion and arm portion are constrained to articulate in a specific axis or axes based on the type or position of the hinge(s). However, the embodiment contains functionally equivalent descriptions of the components of the adjustable tensioning apparatus including the adjustment mechanism, the adjustable mechanism insert, one or more cable, and a tensioning element. The tensioning element in this case represents one type of energy storage element, in this case under tension.

The way the cable or cables (14) are connected to the adjustment mechanism may change how forces are applied on one or more cables, e.g., adding tension to one while decreasing tension on another, or providing equivalent tension to both cables. In the same way, tension may be increased on one side of the cable and decreased on the other side of the cable.

The cables (14) may be connected directly to the arm portion, therefore directly connecting the adjustment mechanism and the arm portion. The cables may also be indirectly attached to either the adjustment mechanism (13) and/or the arm portion. Indirectly attached can mean being connected to described components, e.g. a cable may be indirectly attached to the arm portion by attaching to a tensioning element, wherein the tensioning element is directly, attached to the arm portion. In aspects, these may be connected in line with one another. Such an example is shown in this embodiment, where the cable is indirectly connected from the adjustment mechanism to the arm portion by a tensioning element and anchors.

The anchors (31), as described herein, generally refer to any type of anchor, hook, hook and loop materials, button, screw, knot, fastener, insert or connecting mechanism that exist between components of the tensioning apparatus, proximal portion, and/or arm portion. The location of the anchors on the tensioning apparatus, body portion, or arm portion, may be changed to control the direction of force around the joint. They may be set during fabrication or may be moved by the wearer; user or professional (e.g., physician or clinician) as necessary or desired to change the direction of force.

Energy Storage System

The energy storage element (18), in this example a tensioning element, may comprise rigid, semi rigid, elastic or spring elements individually or in combination. Force may be stored within the energy storage element to generate a torque or force around the desired axis or combination of axes of the joint. The modularity of the device enables this axis of rotation to be changed, either in manufacturing, by the clinician, or by the wearer/user. For example, by positioning the tensioning element on the lower side of the shoulder, dislocation may be prevented. Alternatively, the tensioning element placed anterior to the shoulder may replace the function of the tendon. Both forces can be applied in examples. The direction of the net force vector and positioning of forces around the joint to control range of motion may be modified by positioning of the channels or guides within the proximal portion through which the cable or cables run. Additionally, direction of the net force vector and positioning of forces around the joint to control range of motion may be modified by the shape of the tensioning element, for example an elastomeric band with one point of connection between the proximal and arm portions vs, an elastomeric web with two points of connection to the arras portion vs. an elastomeric sheet continuously connected along the arm portion, which would change the distribution and direction of the net force vector.

The tensioning element (18) can be connected to an arm portion. As such, the body portion can be connected to the arm portion by the tensioning element, which runs across or near the shoulder joint. By example, the tensioning element may be connected to the arm portion with hooks, hook and loop materials, screws, knots, fasteners, inserts or anchors or a melding of material with the tensioning element. The tensioning element and the distal unit may also be manufactured as one continuous piece, for example as a 3D printed or molded thermoplastic material.

In this embodiment and other disclosed embodiments, the tensioning element represents one type of energy storage element, which connects above and below the shoulder. The tensioning element combines with an adjustment mechanism and a cable to operationally generate and control forces around the shoulder joint. The tensioning system in this embodiment is guided by channels and anchors to constrain the movement of the tensioning system and resultant force direction. In aspects, the energy storage element may be one or more of elastomeric bands, webs or other geometries, springs (including but not limited to linear springs, leaf springs, torsion springs, garter springs, and spiral springs) torsion bars, pneumatic elements or springs, electromagnetic elements or springs, pressurized air chambers, coils, hydraulic elements or springs, piezo electric materials, biomimetic materials, or any component that may act as a mechanical energy storage element/spring, or combinations thereof.

A linking element, which is composed of a substantially inelastic material, may be connected to the tensioning element to effectively transmit the forces generated by the tensioning element. The linking element may comprise a line, cable, braided cord, chain, lace, string, band, or the like. The linking element serves to connect the tensioning element to either the adjustment mechanism, the structure of the shoulder orthotic, or both.

One or more channel (29) in the body portion guides the positioning and orientation of the cables, therefore controlling the direction of force. The channel(s) may be unique to the specific model of brace, or it may be custom to the individual based on the precise direction of support that they require. If the path from the adjustment mechanism to the tensioning element is a straight line then a guide element, such as a channel or anchor, for the linking element may not be needed. However, if the path needs to follow a curve then a guide element for the linking element is preferred. For example, if the adjustment mechanism is positioned on the right side of the wearer's chest and the tensioning element is positioned superior to the shoulder, the straight-line path between the two components would intercept the wearer's arm. Thus, in this example, a channel (29) to define the curved path for the linking element may be required. The linking element may be selected to support a force under tension but not compression, under compression but not tension, or under both tension and compression.

In some embodiments, the channel can be built into the shoulder orthosis directly. For example, a channel (29) or tunnel could be created during the composite layup of an orthotic device. It could also be incorporated into the design of a 3D printed device or device produced from other additive methods. t. In other embodiments, a tube or other structure that defines the path of the linking element could be incorporated into the device as a separate affixed component. In yet other embodiments, a sacrificial or temporary material (e.g., a wax tube, a PTFE cord, etc.) could be incorporated during a composite layup to define the guide element in the structure, but would be removed from the article once it had set.

If the force vectors applied to the linking element by the tensioning element and the adjustment mechanism are not in-line (as will be common in practice), there can be an orthogonal vector on the tensioning element forcing it into the channel (29). Thus the material that makes up the channel (29) needs to be strong enough to withstand those orthogonal forces. In addition, the channel (29) should provide a low friction, durable surface for the linking element along which to move, while not creating any damage to the linking element.

In embodiments, the orthotic device may contain a plug or mating surface that the tensioning or linking element can nest in, allowing them to be securely affixed in the orthotic device. In other aspects, a tube, string, pipe, cable, or lace-like structure could be incorporated into at least one end of an elastic tensioning element. The lace-like appendage would act as the linking element to be affixed to the adjustment mechanism. As mentioned above, the linking element connects the energy storage element to the adjustment mechanism and/or the structure of the shoulder orthosis. In some aspects the linking elements that connect the energy storage element to the structure and to the adjustment mechanism are the same (e.g., the linking element that connects the energy storage element to the structure and the linking element that connects the energy storage element to the adjustment mechanism are braided cord). In other aspects the linking elements may differ (e.g., the linking element that connects the energy storage element to the structure is a unitary plug and the linking element that connects the energy storage element to the adjustment mechanism is a braided cord.)

Adjustment Mechanism

The adjustment mechanism (13) can allow the wearer/user to change the magnitude of force within the tensioning element, and therefore the force around the joint based on their need. In some embodiments, the adjustment mechanism allows tension to be increased in one direction, e.g., by clockwise rotation of a dial (19). The tension may be released rapidly by disengaging the dial, e.g., by pulling it out, pushing it in, or pressing a button. In other embodiments, the adjustment mechanism may allow gradual increase or decrease of tension. For example, clockwise rotation of a rotary dial would increase tension, while counterclockwise rotation of the dial would reduce tension, by way of example only. The adjustment mechanism may be a rotary dial, a lever, a switch, a ratchet and pawl mechanism, a pulley, or an electronic adjustment mechanism operated by a controller and/or a motor. The adjustment mechanism may be placed in a preferred position for use that is non-obstructive during activity, but accessible, for example at the rear of the body portion.

In aspects, the adjustment mechanism (13) can have two modes: an increasing of unloading force mode and a releasing of the unloading force mode. In some aspects a third mode is provided: a decreasing of the unloading force mode.

There are examples of mechanisms that can serve as the adjustable element including lever arms, rotating dials, ratcheting handles, pulleys, rack and pinion assemblies, wedges, cams as well as switches, buttons, potentiometers, slides to control powered components such as motors, servos, actuators, and the like. Methods for tailoring the unloading force such as adding or subtracting elastic elements are also possible. Similarly, notched or perforated band/belt could be positioned on a peg, post, or other receptacle to provide the adjustment function.

A non-limiting example of a suitable adjustment mechanism is a tensioning dial (such as those manufactured by BOA™ Technologies of Colorado Springs, Colorado) as the adjustable element and a socket adapted to secure the tensioning dial as the anchoring element. Twisting the tensioning dial winds a lace onto an internal spool. In aspects of certain disclosed applications, the device may require a tensioning dial with greater durability and the ability to generate and maintain greater torque than current on-market tensioning dials, such as those from BOA™ Technologies. In such cases, embodiments of the device may comprise a high-torque tensioning dial (capable of maintaining over 200 in-lb of torque after repeated applications), which is designed to achieve greater degrees of mechanical advantage of at least four-to-one. Such a system may include combinations of multiple planetary gear systems, compound gear systems, or torsion gears. In other aspects, certain disclosed applications of the device may require a tensioning dial or adjustment mechanism that is easier to engage and disengage than current on-market technologies while being capable of maintaining high torque. For example, a tensioning dial that can be disengaged with a push-button mechanism to move pawls or the gear system itself could allow for easier use by individuals suffering from dexterity limitations due to neurological disorder or stroke. In the case where the other end of the lace is connected to an elastic energy storage element, twisting the dial increases the unloading force generated by the Hinge Module, Tension Module, and adjustment mechanism assembly, for example. Pulling on the dial releases the internal ratcheting mechanism of the tensioning dial. In order to secure the adjustable element to the shoulder orthosis, a socket can be incorporated in the frame or support of the orthosis. Preferably the socket has a pathway or guide for the linking element of the energy storage element (a lace, in this example) and optionally a means to secure one end of the anchor.

In other aspects, the shoulder orthosis adjustment mechanism may be a lever, wherein the lever is connected directly or indirectly to the arm and body portions, and the adjustable tensioning mechanism acts upon the lever in a manner that changes the force between the arm and body portion. The lever may further comprise a ratchet system to draw and release tension.

The design of the adjustment mechanism, as well as the positioning on the body portion and arm portion of the orthosis itself, allows for the user to adjust the tension in the device, the weight unloaded from the joint and the stability provided in real time during activity. This is important in order to accommodate the user's desired activity or rehabilitative needs at a given point in time. For example, the adjustment mechanism may be adjusted to low tension while the user has their arm at rest, medium tension while performing everyday activities like cooking, and high tension while the user is lifting a heavy object. The tension may be released rapidly altogether by disengaging the energy storage system by, for example, pulling the adjustment dial out or pressing a button. The user is able to rapidly adjust the level of support based on their current pain level, allowing for an instant feedback loop by which the device's level of support can be optimized to the user need.

By way of example, a proximal fabric (semi-rigid) cuff (11) may anchor the device to the shoulder. The body portion may also be connected to the neck, collar or at another position above the shoulder joint. The body portion may be rigid or semi rigid to fit to the user's shoulder, neck, or any part of the upper body. The arm portion can attach or conform to the user's elbow, hand or any part of the arm or provide additional support and to maximize comfort. The arm portion may be comprised of a rigid or semirigid custom or off the shelf elbow brace or wrist brace. The arm portion may work synergistically with the adjustable tensioning mechanism (13) in order to optimize the joint geometry, modify forces within other lower limb joints such as the wrist, elbow and/or shoulder, and modify arm movement/range of motion.

Overall, the embodiment allows for customization to fit the user's specific need in many aspects. The magnitude of force can be modified by the adjustment mechanism and also by the material properties and geometry of the tensioning element. The direction of force and axis of rotation can be modified by the adjustment mechanism (13), the channel (29) location on the body portion, the location and number of anchor points (31) between the cable (14) and the tensioning element (18), the geometry of the tensioning element, and/or the location of the connection between the tensioning element and the arm portion. Through these mechanisms, rotation can be limited or controlled in one or more of the ML, AP and vertical axes to stabilize, correct, compress or unload the shoulder joint. The device can then therefore be engaged to restore proper shoulder orientation or joint geometry.

Furthermore, the incorporation of hinges in this embodiment allows for important postoperative function where range of motion can be completely limited around one axis of rotation but controlled dynamically around another. For example, embodiments may include a hinge connected to the body portion and arm portion by rigid members comprised of plastic or metal. The hinge may be positioned in the anterior-posterior plane of the joint, therefore allowing a full range of motion around the anterior-posterior axis of the joint while preventing any motion around the other axes of the joint. In this example, the hinge would allow free rotation around. In other embodiments, the hinge may allow for addition of flexion or extension stops that can prevent range of motion in the flee rotation plane between certain degrees of motion. For example, an individual recovering from rotator cuff surgery may be prescribed extension stops that prevent raising of the individual's arms. These extension stops could be removed or reduced in size at a specific stage of recovery. Alternatively, a position lock may be incorporated to lock the shoulder at a specific angle of flexion or extension. The extension or flexion stops, by example, may include wedges, clips, pins and slots, inserts, or wires. The extension or flexion stops may act under compression or tension to limit range of motion. The extension or flexion stops may be rigid to generate a complete stop at a specific range of motion, or they may be semi-rigid (for example an elastomer) to provide a more gradual stop to range of motion. The hinge may be positioned in a different plane or any orientation in order to limit desired range of motion of the joint in one or more axes but allow it in other axes. Similarly, multiple hinges or complex hinges can more specifically tailor the range of motion of the joint to the individual's need. In embodiments, the hinge itself can be moved or adjusted to change the plane in which range of motion is limited.

In aspects, the hinge may conform to the shoulder, arm, chest or other body part in order to mimic the movement of the joint.

Preferred Embodiment: Multi-Axis Rotation Control Shoulder Brace with Force Augmenter Another embodiment is comprised of a body portion and an arm portion that incorporates a tensioning element.

An embodiment of the shoulder brace includes a system of tensioning elements with multiple attachment points. The anchor points of the system can redirect the net forces on the shoulder through this system of tensioning elements. These systems have anchor points on 3 portions of the brace: the torso portion, the bicep portion, and the shoulder joint portion. Using 2 to 3 of these areas allow for a variety of net force vectors ultimately pulling the shoulder in different directions. Multiple elastic and/or inelastic cables can be attached to these 3 anchor points to limit or completely eliminate mobility of the shoulder joint in certain directions.

One example of this embodiment is a one cable system extending from the torso portion, through the shoulder joint portion, and finally anchored at the superior bicep portion. This system secures the joint by limiting the mobility of the shoulder away from the body. Using an inelastic cable would completely restrict the joint in this system. This system could also include additional elastic cables anchored in the front or back of the torso region to allow for a user adjusted restriction of forward and backward motion. Attaching an elastic element with an adjustable dial to the rear of the torso region limits the user from moving the arm forward, but does not completely immobilize the user. This in addition to the cable extending through the other two anchor systems secures the joint with two different force vectors of possibly different forces.

Another example of this embodiment is securing a cable to the anchor system through the anterior part of the bicep portion of the brace and extending it through an anchor point on the under arm of the brace and with the other side attached to the opposite side torso portion. In addition, a cable could be secured to the superior part of the bicep portion on one side and extended through to the shoulder joint portion and ultimately anchored on the opposite side torso region. Having a system with these two cables being elastic in region would result in a net force vector into the body at all times. When a user reaches their arm above their head, the force would pull the arm into the body, limiting the ability for the shoulder to dislocate and damaging the joint.

Methods of Use

The device in embodiments described herein are designed to maximize ease of use and comfort for the user/wearer. The device can be comprised of lightweight, durable materials including but not limited to fabrics, plastics, elastomers, and 3D printed thermoplastics. In aspects, the user/wearer can easily and rapidly (within 10 seconds just by way of example) don and doff the device. In some embodiments, the body portion and/or arm portion may be flexible so that the user/wearer can stretch the material to slide their arm and shoulder into the device. In other embodiments, the device may contain an opening, example made of hook and loop, so that the user can open and close the device to don and doff. The device can be manufactured to have a low profile, in order to fit comfortably and conveniently within the user's clothing. In other embodiments, the device itself may substitute for the user's clothing and function as clothing with an integrated tensioning mechanism.

In the various embodiments of the present disclosure, the magnitude and direction of force applied (or resistance or tension generated in the orthosis) can readily be tailored to the user/wearer based on their size, weight, joint geometry, injury, and/or desired activity. Braces as described herein can be light-weight, robust, tow-profile, and well-fitting to users. Unlike braces in the prior art, those disclosed herein can be narrow and lightweight to be worn within clothing, which may be required for high-performance athletics but is not enabled by many existing braces on the market.

The various embodiments of the shoulder brace of the present disclosure can be used, by way of non-limiting examples: prophylactically to prevent injury; to reduce joint pain (e.g. during physical exercise or athletic competition); to rehabilitate existing injuries; postoperatively (high tension braces to immobilize or limit movement of the joint to a comfortable level within one or more desired range of motion); to assist or augment movement within a desired direction (e.g. in a direction limited by muscle, tendon or ligament deficiency or damage), and to provide stability and alignment to the joint.

The device described in embodiments can correct the position of the arm relative to the user's shoulder to restore proper range of motion or functionality. In other uses, the user/wearer may apply the device in embodiments to augment movement of the joint in one or more directions. For example, an athlete intending to increase arm-lifting force would use a device similar containing an elastomeric tensioning element on the proximal side of the shoulder. The user would 1) don the device, for example the device shown in the figures, 2) optionally adjust the position of the device, and 3) increase force in the tensioning element using the adjustment mechanism. Such an embodiment would reduce strain on the shoulders during overhead work, for example.

in other uses, the user/wearer may apply the device in embodiments to support recovery or improve range of motion of the muscle, ligament, tendon, cartilage, and/or bone of the shoulder post-operation or post-injury. Additionally, the user may use the device to maintain joint function during the recovery period while protecting the joint from further damage. For example, for a user/wearer with lateral tendon tear, the user/wearer would 1) don the device, for example shown in the figures, 2) optionally adjust the position of the device, and 3) increase force in the tensioning element (18) using the adjustment mechanism (13) to prevent inversion while allowing range of motion in other axes, therefore protecting the lateral ligaments from further strain.

The embodiments described are capable of unloading a region of the shoulder joint based on the direction and magnitude of force generated by the tensioning element. This can be achieved in one aspect by generating a counterforce on one side of the shoulder to reduce contact force on the opposite side. For example, by engaging an elastomeric tensioning element on the anterior side of the user's shoulder, the posterior side of the shoulder will be separated. This will separate the lateral side of the shoulder, and act as a spring to reduce the force within that region of the joint upon impact with the ground at each step. The mechanism can also reduce forces in an osteoarthritic or damaged region of the joint by altering the user's range of motion. For example, by engaging the tensioning element to support dorsiflexion, generating a torque around the ML axis of the shoulder, the posterior region of the shoulder will contact the ground force and experience the initial impact. In this way, the anterior region of the shoulder can be shielded from more significant forces that the user would normally experience without use of the device. In the case of an individual with shoulder OA in the anterior region of their joint, this would act to reduce their pain during activity.

The device is designed such that it may be worn over or under the user's clothing. These embodiments may also be equipped with at least one sensor that collects senses information on rotation, range of motion, biomechanics, and health of the joint, by way of example, Using a processor running one or more software application, this information may then be used to tailor or tune the device more precisely to the needs of the user/wearer, or inform a medical professional of information helpful in making decisions on a rehabilitation or treatment regimen, including decisions related to surgical procedures and joint implants. The device can also augment the function and performance of the joint post-operatively, as well as complement the function of an implanted device or component, actively or passively.

Integration With Other Upper Body Orthotics and Prosthetics

In addition to controlling forces around the shoulder joint, the mechanism of multi-axis rotational control may be achieved across the elbow, wrist, neck or back depending on the positioning of tensioning systems, the anchoring of tensioning systems, and the position and design of hinges (and corresponding rotational degrees of freedom) throughout the device. Rotation of the joint around any axis may be limited, controlled, prevented, or supported at different stages of movement to better mimic the natural function of the joint, improve user comfort, or provide the desired outcome of joint unloading while minimizing limitations to the user's natural range of motion. The magnitude of rotational control around each axis may change dynamically with varying degrees of flexion, extension or rotation in order to control overall arm movement in a highly controlled manner. In aspects, the rotation control mechanism and function may be performed by a modular attachment, which can be combined with the shoulder orthosis component, or any other joint brace comprising adjustable tensioning systems, including existing elbow, neck, wrist or back braces that lack adjustable rotation control mechanisms.

A shoulder-elbow orthosis (or a shoulder-elbow-wrist orthosis) may comprise an elbow orthosis component that contains an adjustable tensioning mechanism, separate from or continuous with the tensioning systems described in the shoulder orthosis component. In other embodiments, the unloading and assistive shoulder orthosis described may be extended distally to the elbow orthosis but also to optionally employ an adjustable tensioning hinge system, wherein the elbow joint can experience assistance and/or resistance that is optionally adjustable by the user with an adjustment mechanism. The position and orientation of the tensioning or compression system may be modified based on the type, location, and the severity of the body injury. The device may optionally be extended shoulder and elbow orthosis, where the attachment between the orthoses is rigid, semi-rigid, or has a built-in rotation system to allow for natural range of motion between the shoulder and elbow to perform specific tasks. The assistance and resistance may be fixed, dynamic with flexion, or adjustable and/or variable at any point in the system of the orthoses. The rotation mechanism may also be fixed, dynamic, or adjustable and/or variable, and all can be tailored to the needs of the patient. The tensioning system of the elbow component may be applied to alleviate tennis elbow or support healing during elbow strain or fracture.

In embodiments, the tensioning systems of the shoulder and elbow components may be connected directly or indirectly. For example, the user may add tension to the shoulder orthosis component to further support the shoulder to prevent dislocation, which also tensions the elbow system to support extension and alleviate pressure in the joint. The connected tensioning systems may optionally contain pulley or gear systems that determine the relationship of forces and/or distance moved by the connected tensioning systems. For example, a gear system between the shoulder orthosis and elbow orthosis tensioning systems could allow for a lesser force applied around the elbow joint and a greater force applied around the shoulder joint while adjusting only one interconnected tensioning system. Additionally, gear, ratchet or other mechanisms may be used to engage the shoulder orthosis and/or elbow orthosis tensioning systems at specific points, for example at a certain range of rotation or elbow flexion. This could be achieved by using a distracting hinge in one of the hinge mechanisms for the elbow orthosis component, allowing for additional unloading forces based on the flexion of one of the joints, while still maintaining an interconnected tensioning system between the two joints. For example, a linear ratchet mechanism could be applied so that when a specific level of tension is sustained by the shoulder orthosis tensioning system, the elbow orthosis tensioning system will engage to support extension. Tailored differences in the forces applied or path length of the tensioning elements may be achieved by applying different types of tensioning elements, for example elastic bands of different material properties, in each tensioning system to achieve the desired properties for the application. For example, use of an elastomer or spring with a lower Young's Modulus in the elbow orthosis tensioning system and an elastomer or spring with a higher Young's Modulus in the shoulder orthosis tensioning system would lead to different magnitudes of applied force around the shoulder and elbow joints while using one continuous, in-line adjustment mechanism.

In other aspects, mechanisms for joint distraction may be incorporated into regions of the shoulder orthosis to separate or unload regions of the joint. Joint distraction is defined as applying a force to temporarily unload the joint space and cartilage by eliminating contact between the joint surfaces. This can be accomplished through elements in compression or elements that generally increase the distance across the joint upon articulation. The Shoulder Orthosis may incorporate a distracting hinge comprised of teethed gears, cams, or articulating members of variable radii, wherein the distance between the gear centers increases or decreases through flexion, extension or rotation. The gears may be connected by a hinge cap and may contain slots and pins to guide the path of distraction. Alternatively, the distraction hinge may incorporate a series of two or more gear systems, wherein a second gear system engages and articulates at a specific range of flexion and provides a greater distance, therefore a distracting force, between the upper and lower portions of the orthosis. This mechanism may be described as a compound gear system. Other embodiments and methods of distracting the joint include four bar mechanisms, spring mechanisms, pneumatic or motorized pistons, or telescoping mechanisms. Similar distraction hinge mechanisms may be present in either the elbow, shoulder or back portions of the shoulder orthosis. The distracting hinge provides a distracting force across the shoulder joint in order to separate or unload the joint. Hinges with different radii on opposite sides of a brace (e.g. the anterior and posterior sides) may also create a rotation effect that can change the joint biomechanics in a desirable way. Furthermore, the distracting hinge may be aligned with the patient anatomy and the hinge may conform to the patient anatomy in a way where the distraction engages and or increases in the areas of joint flexion corresponding with the patients' varying need for unloading, creating a dynamic unloading system that is proportional with anatomical unloading necessity. The various configurations of shoulder orthoses comprise an arm portion and a body portion that are connected via a hinge assembly on one or both sides of the joint.

In other embodiments, the hinge may comprise a "double-spooner" hinge joint that conforms to the patient's shoulder around the glenohumeral joint, which cup and stabilize the joint while also preventing migration of the device in the proximal or distal direction. Rather than a rigid chest portion, tensioning bands encompass the joint around the articulating, conforming hinges to generate a torque around the joint. The direction of the torque (clockwise or counter-clockwise) would be determined by the positioning of the bands themselves around the hinge while the magnitude of force is controlled by a tensioning dial.

Another hinge embodiment connects arm and body portions with a uni- or poly-centric hinge, and the parts of the hinge attached to the arm portion and the body portions may slide so that the hinge does not bind. Tensioning elements can be run over the top of the hinge. The height and shape of the hinge generates leverage upon articulation to increase or decrease force within the tensioning elements, generating a torque or compressive force around the joint. The hinge may or may not incorporate an adjustment mechanism, and force around the joint will increase or decrease as a function of the joint range of motion.

It should be understood that the described embodiments are by example only. The same embodiments may incorporate springs or other energy storage elements to generate force across the joint in a similar fashion to the tensioning elements described, Additionally, adjustable compression mechanisms may substitute for the adjustable tensioning mechanisms in order to perform similar functions as described in the multi-axis rotation control brace.

In other embodiments, the shoulder orthosis may include magnets for fixation of parts, for generation of an electromagnetic field that can be controlled by an actuator in order to generate forces around a joint, or to generally modify, limit or control joint geometry. In aspects, the magnetic system or electromagnetic field can interact with an implant within the joint. The joint implant and the orthosis may contain sensors that interact, in order to affect function, adjustment of the tensioning apparatus, or generally provide data to the user/wearer or clinician for rehabilitative or other purposes described herein.

Embodiments of the invention also include a computer readable medium comprising one or more computer files comprising a set of computer-executable instructions for performing one or more of the calculations, steps, processes, and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor 24 may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e., processor) and a form of computer readable memory which may include random-access memory (RAM) or read-only memory (ROM). The computer-executable instructions can be embedded in computer hardware or stored in the computer-readable memory such that the computer or device may be directed to perform one or more of the calculations, steps, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a. network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection. In another embodiment, the user interface may be managed and controlled through an App or program on a phone, tablet, or other portable electronic device.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features, Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all the references cited in this disclosure are each individually incorporated by reference herein in their entirety and as such are intended to provide an efficient way of supplementing the enabling disclosure of this invention as well as provide background detailing the level of ordinary skill in the art.

The invention claimed is:

1. A shoulder orthosis comprising:

an arm portion for securing to an arm of a wearer;

a body portion for securing to a body or another body part of the wearer; and a tensioning system comprising an adjustment mechanism and one or more cables, wherein the one or more cables are operatively connected to the adjustment mechanism, wherein the one or more cables directly or indirectly connect the arm portion to the body portion, and wherein the one or more cables are positioned across a shoulder joint of the wearer; wherein the adjustment mechanism is configured to allow the wearer to adjust and/or control a force or forces across, between, or around the shoulder joint of the wearer; wherein the adjustment mechanism is configured to generate a mechanical advantage when operated to increase the force or forces across, between, or around the shoulder joint of the wearer; and wherein the position of the one or more cables across the shoulder joint at least one of controls, governs, or determines, a direction or directions of the force or forces across, between, or around the shoulder joint of the wearer.

2. The shoulder orthosis of claim 1, further comprising a tensioning element or a compression element, wherein the tensioning element or the compression element is operationally attached to or continuous with the arm portion, the body portion, or both, or wherein the tensioning or compression element is provided between the arm portion and the body portion.

3. The shoulder orthosis of claim 2, wherein the tensioning element or the compression element is comprised of one or more of: one or more elastomeric material, one or more band, one or more web, one or more webbing, one or more spring, one or more piston, one or more electromagnetic material, one or more hydraulic element, one or more pneumatic element, or one or more energy storage element.

4. The shoulder orthosis of claim 1, wherein the tensioning system further comprises at least one elastomeric band, elastomeric web, or elastomeric material.

5. The shoulder orthosis of claim 1, further comprising one or more anchors or anchor points that can be placed in varied positions, wherein the one or more anchors or anchor points direct the force or forces across, between, or around the shoulder joint of the wearer.

6. The shoulder orthosis of claim 5, wherein the one or more anchors or anchor points are constrained to move on a track system, wherein the track system allows for the one or more anchors or anchor points to be locked at different positions in order to set an orientation of the tensioning system and an overall direction of a net force around the shoulder joint.

7. The shoulder orthosis of claim 1, further comprising one or more channels, wherein the one or more channels direct the force or forces across, between, or around the shoulder joint of the wearer.

8. The shoulder orthosis of claim 1, wherein the arm portion and the body portion of the shoulder orthosis are connected by one or more hinges.

9. The shoulder orthosis of claim 8, further comprising one or more slots, wherein the one or more slots are optionally contained within at least one side of the one or more hinges.

10. The shoulder orthosis of claim 8, further comprising flexion stops, extension stops, or a positional lock to limit the range of motion of the shoulder joint of the wearer in one or more axes.

11. The shoulder orthosis of claim 1, wherein the arm portion of the shoulder orthosis connects to an elbow orthosis, wherein the elbow orthosis optionally connects to a wrist or hand orthosis, wherein the wrist or hand orthosis optionally connects to a finger orthosis.

12. The shoulder orthosis of claim 1, wherein the body portion of the shoulder orthosis at least one of connects to or integrates with at least one of a back orthosis, a spine orthosis, a neck orthosis, or a shoulder orthosis, on an opposite shoulder of the wearer.

13. The shoulder orthosis of claim 1, wherein the adjustment mechanism comprises a motor for motorized adjustment of the force or forces across, between, or around a shoulder joint of the wearer, and wherein the force or forces generated by the tensioning system are adjusted automatically, partially automatically, or manually.

14. The shoulder orthosis of claim 1, further comprising one or more sensors, wherein the one or more sensors collect information about at least one of wearer compliance for wearing the shoulder orthosis, range of motion of a shoulder of the wearer, biomechanical alignment and function of the shoulder of the wearer, stability of the shoulder of the wearer, relative position of the shoulder of the wearer, movement patterns of the shoulder of the wearer, shoulder joint health of the wearer, or wearer biometric data.

15. The shoulder orthosis of claim 14, wherein the information is used to at least one of design, re-design, or modify the shoulder orthosis, to apply a functionality of one or more external or implantable devices, or to apply or adjust the force or forces across, between, or around the shoulder joint of the wearer.

16. The shoulder orthosis of claim 1, wherein the shoulder orthosis is partially or mostly integrated with or within a shirt, a jacket, a coat, or other clothing garment.

17. The shoulder orthosis of claim 1, wherein the shoulder orthosis is affixed to the shoulder of the wearer using one or more of a rigid material, a semi-rigid material, an inelastic material, or an elastic material, wrapped around part or all of the shoulder of the wearer at a first part of the shoulder and attached to the shoulder orthosis at a second part of the shoulder.

18. The shoulder orthosis of claim 1, wherein the tensioning system further comprises one or more adjustable springs and/or one or more elastomeric element, and wherein the one or more adjustable springs and/or the one or more elastomeric element store a compression force or forces.

19. The shoulder orthosis of claim 1, further comprising rigid, semi-rigid, or flexible materials or plates, wherein the rigid, semi-rigid, or flexible materials or plates support or interact with one or more of a chest of the wearer, a back of the wearer, the shoulder of the wearer, or an opposite shoulder of the wearer, to stabilize either or both of the arm portion and the body portion of the shoulder orthosis.

20. The shoulder orthosis of claim 19, wherein the rigid, semi-rigid, or flexible materials or plates are designed to fit the shoulder of the wearer based on measurements from a three-dimensional scan of at least one of the wearer, a joint of the wearer, the shoulder of the wearer, the shoulder joint of the wearer, a body part of the wearer, a body of the wearer, an arm of the wearer, or a back of the wearer.

21. The shoulder orthosis of claim 19, wherein the rigid, semi-rigid, or flexible materials or plates comprise modifiable channels or modifiable pathways to direct or re-direct the force or forces in a desired orientation or direction between the arm portion and the body portion of the shoulder orthosis.

22. The shoulder orthosis of claim 1, further comprising one or more sensors, wherein the adjustment mechanism is motorized, wherein information from the one or more sensors is communicated to a computer processor, wherein the computer processor is located in or on the shoulder orthosis or remote from the shoulder orthosis, and wherein the force or forces provided by the tensioning system are automatically adjusted by the motorized adjustment mechanism based on instructions provided to the motorized adjustment mechanism from the computer processor, wherein the instructions are based on the information communicated by the one or more sensors to the computer processor.

23. The shoulder orthosis of claim 1, wherein a lever is connected directly or indirectly to the arm portion and the body portion, and wherein the tensioning system acts upon the lever in a manner that changes the force or forces between the arm portion and body portion.

24. A computer-implemented method of manufacturing a custom shoulder orthosis, the method comprising the following steps:

a. providing a three-dimensional ("3D") scan of a shoulder joint;

b. modeling a force or forces in the shoulder joint based on the 3D scan, user anatomical features, user-reported information, or combinations thereof;

c. designing a simulated digital shoulder orthosis with assistive and/or corrective forces as determined from the modeled force or forces; and d. fabricating the shoulder orthosis device.

25. A shoulder orthosis system comprising:

an arm portion for attaching to an arm of a wearer;

a body portion for attaching to a body of the wearer;

one or more connectors between the arm portion and the body portion for connecting the arm portion to the body portion;

one or more attachment points on both the arm portion and the body portion for attaching the one or more connectors; and a locking mechanism, wherein the locking mechanism is configured to generate a tension force or forces across, between, or around a shoulder joint of the wearer, and wherein the locking mechanism is configured to one or more of, hold tension force or forces, increase tension force or forces, decrease tension force or forces, maintain tension force or forces, or release tension force or forces, in or within the one or more connectors;

wherein the locking mechanism is further configured to generate a mechanical advantage when operated to increase the tension force or forces across, between, or around the shoulder joint of the wearer;

wherein the one or more connectors are operatively connected to the locking mechanism, wherein the one or more connectors directly or indirectly connect the arm portion to the body portion, and wherein the one or more connectors are positioned across the shoulder joint of the wearer;

wherein applying a tension force or forces, in a superior direction of the shoulder joint of the wearer and/or the shoulder orthosis system, on the one or more connectors, generates rotation around at least two of an anterior-posterior axis, a lateral-body axis, and a medial-lateral axis; and wherein a location of the one or more attachment points on the arm portion, the body portion, or both, at least one of controls, governs, or determines, a direction or directions of the tension force or forces.

26. The shoulder orthosis system of claim 25, further comprising one or more elastomeric element provided between the arm portion and the body portion and attached to the one or more connectors.

27. A shoulder orthosis comprising:

an arm portion for attaching to an arm of a wearer;

a body portion for attaching to a body of the wearer;

a cam or pulley element connected to the body portion and positioned above a shoulder joint of the wearer; and a tensioning apparatus comprising an adjustment mechanism and one or more cables directly or indirectly connecting the arm portion to the body portion, wherein the one or more cables are positioned across a shoulder joint of the wearer, and wherein the one or more cables are operatively connected to the adjustment mechanism;

wherein the one or more cables run over the cam or pulley element;

wherein the adjustment mechanism is configured to allow the wearer to adjust and/or control a force or forces across, between, or around the shoulder joint of the wearer;

wherein the tensioning apparatus is configured to generate a mechanical advantage when operated to increase the force or forces across, between, or around the shoulder joint of the wearer;

wherein the position of the one or more cables across the shoulder joint of the wearer at least one of controls, governs, or determines, a direction or directions of the force or forces across, between, or around the shoulder joint of the wearer; and wherein rotating the adjustment mechanism or a portion of the adjustment mechanism is operative to cause the one or more cables to be drawn over the cam or pulley element, thereby providing the force or forces that raise the arm portion in a direction relative to the body portion.

28. The shoulder orthosis of claim 27, wherein the tensioning apparatus comprises a tensioning element, and wherein the tensioning element runs over the cam or pulley element and directs and/or amplifies the force or forces in the superior direction.

29. The shoulder orthosis of claim 28, wherein the tensioning element runs through one or more anchor points to direct and/or amplify the force or forces in the superior direction.

30. A shoulder orthosis comprising:

an arm portion for attaching to an arm of a wearer;

a body portion for attaching to a body of the wearer; and at least one tensioning element, elastomeric band, elastomeric web, or elastomeric material, connecting the arm portion to the body portion, wherein the at least one tensioning element, elastomeric band, elastomeric web, or elastomeric material, exert a force or forces along one or more axes of rotation between the arm portion and the body portion;

wherein the force or forces are variable with movement of the wearer;

wherein a direction and a magnitude of the force or forces is tailored to the wearer based on at least one of an injury type suffered by the wearer to be treated by the shoulder orthosis, a severity of an injury suffered by the wearer to be treated by the shoulder orthosis, or a morphology of a shoulder joint of the wearer to be treated by the shoulder orthosis.

31. A shoulder orthosis for a shoulder joint comprising:

an arm portion for securing to an arm of a wearer;

a body portion for securing to a body or another body part of the wearer; and a compression mechanism comprising (a) a distracting hinge directly or indirectly connecting the arm portion to the body portion, and (b) at least one adjustment mechanism;

wherein the distracting hinge is comprised of one or more pairs of gears, and wherein the one or more pairs of gears upon articulation generate a variable degree of distance between the arm portion and the body portion at different ranges of motion of the distracting hinge, the shoulder of the wearer, or the shoulder orthosis;

wherein the distracting hinge is positioned across the shoulder joint of the wearer;

wherein the adjustment mechanism is configured to allow the wearer to adjust and/or control a force or forces across, between, or around the shoulder joint of the wearer;

wherein the compression mechanism is configured to generate a mechanical advantage when operated to increase the force or forces across, between, or around the shoulder joint of the wearer; and wherein the position of the distracting hinge across the shoulder joint of the wearer at least one of controls, governs, or determines, a direction or directions of the force or forces across, between, or around the shoulder joint of the wearer.

32. The shoulder orthosis of claim 31, wherein the distracting hinge is comprised of a polycentric hinge having gears of variable radii, wherein the variable radii gears generate a distraction force across or around a shoulder joint of the wearer.

33. The shoulder orthosis of claim 31, wherein the distracting hinge is comprised of a four bar mechanism.

* * * * *